United States Patent [19]

Conciatori et al.

[11] Patent Number: 4,514,553
[45] Date of Patent: Apr. 30, 1985

[54] THERMOSET RESIN PRODUCED FROM ANISOTROPIC HEAT-CURABLE ACRYLIC-TERMINATED MONOMERS

[75] Inventors: Anthony B. Conciatori, Chatham; Eui W. Choe, Randolph; Gerald Farrow, New Providence, all of N.J.

[73] Assignee: Celanese Corporation, New York, N.Y.

[21] Appl. No.: 576,554

[22] Filed: Feb. 3, 1984

Related U.S. Application Data

[62] Division of Ser. No. 381,598, May 24, 1982, Pat. No. 4,452,993.

[51] Int. Cl.$^3$ .............................................. C08F 20/30
[52] U.S. Cl. ................................................. 526/323.1
[58] Field of Search ...................................... 526/323.1

Primary Examiner—Paul R. Michl
Attorney, Agent, or Firm—Burns, Doane, Swecker & Mathis

[57] ABSTRACT

Novel heat-curable acrylic-terminated monomers are provided which exhibit an optically anisotropic melt phase at a temperature which enables it to undergo melt processing in the formation of molded articles, etc. The monomers are capable of being heat-cured at temperatures in excess of the melt processing temperatures to produce a thermoset self-reinforced composite. The monomer may, for example, consist essentially of the reaction product of p-acryloyloxybenzoic acid and a difunctional aromatic moiety in a molar ratio of about 2:1.

16 Claims, No Drawings

THERMOSET RESIN PRODUCED FROM ANISOTROPIC HEAT-CURABLE ACRYLIC-TERMINATED MONOMERS

This application is a division of application Ser. No. 381,598, filed May 24, 1982, now U.S. Pat. No. 4,452,993.

BACKGROUND OF THE INVENTION

The present invention is directed to anisotropic heat-curable monomers.

Multi-functional heat-curable monomers are known which can be employed in the production of thermosetting composites such as, for example, epoxy-based compositions. However, one disadvantage with such known thermosetting compositions is that they tend to shrink to an undesirable degree subsequent to the cross-linking reaction.

It is therefore desirable to provide heat-curable monomers which can be employed in the production of thermosetting resins and which exhibit a reduced tendancy to shrink upon curing.

It would also be desirable to provide heat-curable monomers which exhibit self-reinforcing characteristics as a result of molecular orientation in the cross-linked resin.

OBJECTS AND SUMMARY OF THE PRESENT INVENTION

It is therefore an object of the present invention to provide novel heat-curable monomers which exhibit reduced tendency to shrink upon curing.

It is also an object of the present invention to provide heat-curable monomers which permit a cross-linked resin to be formed therefrom which exhibits self-reinforcing characteristics due to molecular orientation in the resin.

In accordance with the present invention, there are thus provided novel heat-curable acrylic-terminated monomers capable of forming an anisotropic melt phase of the formula:

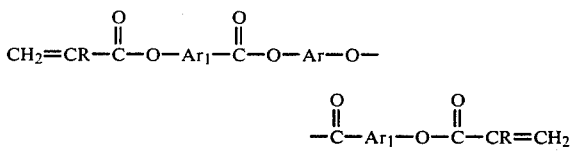

wherein Ar is a divalent radical comprising at least one aromatic ring, $Ar_1$ is a divalent radical selected from the group consisting of phenylene, naphthylene, biphenylene and mixtures thereof and R is selected from the group consisting of hydrogen and methyl.

In accordance with another aspect of the present invention, there are thus provided cross-linked polyester resins comprised of the above-described monomers.

DETAILED DESCRIPTION OF THE INVENTION

It has been surprisingly and unexpectedly discovered that the heat-curable monomers of the present invention can be employed with significant advantage in the production of thermosetting polyester resins. Such resins would be expected to exhibit reduced shrinkage subsequent to being cured due to the fact that such monomers are capable of forming an anisotropic melt phase upon being heated to the melting temperature of the monomer.

Unlike monomers commonly encountered in the prior art, the monomers of the present invention are capable of forming an anisotropic melt phase whereby an atypical degree of order is manifest in the molten monomer. The monomer readily forms liquid crystals in the melt phase and accordingly exhibits a high tendency for the monomer chains to orient in the shear direction, with such anisotropic properties being exhibited at temperatures which are amenable for melt processing to form shaped articles. Such order in the melt may be confirmed by conventional polarized light techniques whereby crossed polarizers are utilized. The anisotropic melt phase may be confirmed by the use of a Leitz polarizing microscope at a magnification of 40X with the sample on a Leitz hot stage and under nitrogen atmosphere. The monomer melt is optically anisotropic, i.e., it transmits light when examined between crossed polarizers. The amount of light transmitted increases when the sample is optically anisotropic even in the static state.

The monomers of the present invention can be denoted by the formula:

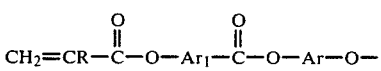

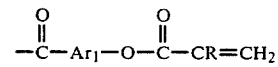

wherein Ar is a divalent radical comprising at least one aromatic ring, $Ar_1$ is a divalent radical selected from the group consisting of phenylene, naphthylene, biphenylene and mixtures thereof and R is selected from the group consisting of hydrogen and methyl.

By way of example, the divalent radical Ar may include but is not limited to the following:

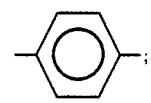
(I)

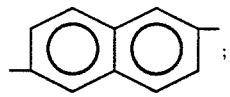
(II)

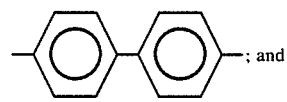
(III); and

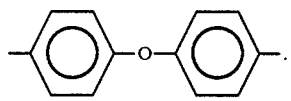
(IV).

At least some of the hydrogen atoms present upon one or more of the aromatic rings in the divalent radicals Ar and $Ar_1$ optionally may be replaced by a substituent selected from the group consisting of an alkyl group of 1 to 4 carbon atoms, an alkoxy group of 1 to 4 carbon atoms, halogen, phenyl, substituted phenyl and mixtures thereof, provided such substitution does not ultimately prevent the monomer from forming an anisotropic melt phase. It is recognized, however, that such substitution may alter the temperature at which the phase transitions occur for the monomer (i.e., the transition from a solid to an anisotropic melt and from an anisotropic melt to a polymerized/cross-linked composition).

More specifically, the monomers of the present invention may include but are not limited to hydroquinone-bis-acryloyloxybenzoate, 4,4'-biphenol-bis-acryloyloxybenzoate, chlorohydroquinone-bis-acryloyloxybenzoate, methylhydroquinone-bis-acryloyloxybenzoate, 4,4'-oxybiphenol-bis-acryloyloxybenzoate and 2,6-dihydroxynaphthalene-bis-acryloyloxybenzoate.

As noted previously, the monomers of the present invention are capable of forming an anisotropic melt phase upon being heated to the necessary phase transition temperature. The monomers will retain such anisotropic characteristics upon being heated to increasingly higher temperatures whereupon the monomer will begin to polymerize and/or cross-link at a temperature in excess of the melting temperature of the monomer and form a thermosetting polymeric resin. The resin advantageously retains the high degree of orientation exhibited by the monomer molecules prior to such polymerization, with the orientation of the molecules in the resin providing a self-reinforcing effect.

Exemplary phase transition temperatures for certain novel monomers of the present invention are set forth below in Table I:

TABLE I

Phase Transitions of Exemplary Anisotropic Multifunctional Monomers

| Ar Employed[a] | Transition Temperature from Solid to Anisotropic Melt | Transition Temperature from Anisotropic Melt to Polymerization |
| --- | --- | --- |
| phenylene | 154° C. | 90° C. |
| chlorophenylene | 134° C. | 166° C. |
| methylphenylene | 60° C. | 175° C. |
| naphthylene | 142° C. | 167° C. |
| biphenylene | 130° C. | 150° C. |
| oxy-biphenylene | 97° C. | 175° C. |

[a]$Ar_1$ is phenylene in each instance

It is interesting to note that an acrylic-terminated monomer having the following structure does not exhibit anisotropic properties in the melt phase in contrast to the monomers of the present invention even though it is similar in structure:

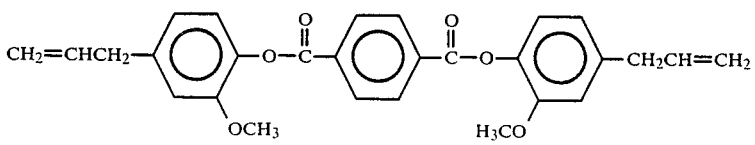

The above monomer will, in contrast to the monomers of the present invention, form an isotropic melt at a temperature of 175° C. and polymerize at a temperature of 250° C.

The monomers of the present invention may be formed by a variety of ester-forming techniques such as, for example, whereby p-acryloyloxy benzoic acid and a difunctional aromatic moiety possessing hydroxyl groups are reacted which, upon condensation, form the requisite monomer. The acid and the difunctional aromatic moiety are reacted in a molar ratio ranging from about 2:0.5 to about 2:1. The organic monomer compounds may be reacted in the absence of a heat exchange fluid via a melt acidolysis procedure. They, accordingly, may be heated initially to form a melt solution of the reactants with the reaction continuing as said polymer particles are suspended therein. A vacuum may be applied to facilitate removal of volatiles formed during the condensation (e.g., acetic acid).

The monomers of the present invention can be molded or otherwise melt processed and then heat cured to yield a polymerized composite of high strength due to the self-reinforcing characteristics of the oriented molecules. The composite will also exhibit desirable thermal and chemical stability. The monomers can be melt processed to form a variety of shaped articles by conventional extrusion and injection molding techniques. Such molding compositions may optionally include various types of fillers (e.g., talc) in amounts of about 1 to 60 percent by weight as well as various types of reinforcing agents (e.g., glass fibers) in amounts of about 1 to 60 percent by weight.

The monomers of the present invention may also be employed as protective coatings on various substrates in the form of the cross-linked resin. The monomers can also be employed as the matrix material for a web of infusible fibers such as glass fibers wherein the monomer is applied to the web in an anisotropic melt state and subsequently heat-cured. Such methods are well known in the art and will not be discussed in greater detail herein.

The invention is additionally illustrated in connection with the following Examples which are to be considered as illustrative of the present invention. It should be understood, however, that the invention is not limited to the specific details of the Examples.

EXAMPLE 1

A solution of p-hydroxybenzoic acid (38.15 grams, 0.276 mole) in 100 milliliters of ether and 1.0 liter of methylene chloride is formed and placed in a 3 liter three-necked flask equipped with a condenser and a stirrer under argon. Acryloyl chloride (25 grams, 0.276 mole) is added to the flask and triethylamine (27.9 grams, 0.276 moles) is added dropwise. A yellow precipitate forms immediately and the mixture is allowed to stand overnight, after which it is diluted with 1.0 liter of water. The organic layer formed is separated, washed with water and evaporated to yield a yellow solid. Recrystallization from aqueous ethanol yields 13.25 grams of p-acryloyloxybenzoic acid.

p-acryloyloxybenzoic acid (19.2 grams, 0.1 mole) is placed in a three-necked flask equipped with a nitrogen inlet and outlet, mechanical stirrer and distillation head. Thionyl chloride (100 milliliters) is slowly added to the flask and the resulting admixture is heated to 70° C. to convert the p-acryloyloxy benzoic acid to the corresponding acid chloride. Excess thionyl chloride is then removed by distillation, with a vacuum also being employed to remove as much of the thionyl chloride as possible. The reaction mixture is cooled to 35° C. and hydroquinone (4.4 grams, 0.04 mole) in methylene chloride (as a solvent) is added. Triethylamine as an acid acceptor (25 milliliters) is also added slowly and the mixture is stirred for 16 hours. The methylene chloride is then evaporated on a rotary evaporator. The residue is washed with water and 5 percent sodium bicarbonate, rewashed with water and dried in air to yield 14.8 grams of hydroquinone-bis-acryloyloxybenzoate.

EXAMPLE 2

A monomer is prepared in the same manner as in Example 1 with the exception that 2,6-dihydroxynaphthalene (6.4 grams, 0.04 mole) is substituted for hydroquinone to yield 2,6-dihydroxynaphthalene-bis-acryloyloxybenzoate.

EXAMPLE 3

A monomer is prepared in the same manner as in Example 1 with the exception that 4,4'-dihydroxybiphenyl (7.44 grams, 0.04 mole) is substituted for hydroquinone to yield 16.2 grams of biphenol-bis-acryloyloxybenzoate.

EXAMPLE 4

A monomer is prepared in the same manner as in Example 1 with the exception that methylhydroquinone (4.96 grams, 0.04 mole) is substituted for hydroquinone to yield 11.2 grams of methylhydroquinone-bis-acryloyloxybenzoate.

EXAMPLE 5

A monomer is prepared in the same manner as in Example 1 with the exception that chlorohydroquinone (5.78 grams, 0.04 mole) is substituted for hydroquinone to yield 14.3 grams of chlorohydroquinone-bis-acryloyloxybenzoate.

EXAMPLE 6

A monomer is prepared in the same manner as in Example 1 with the exception that 4,4'-oxydiphenol (8.09 grams, 0.04 mole) is substituted for hydroquinone to yield 21.9 grams of 4,4'-oxybiphenol-bis-acryloyloxybenzoate.

EXAMPLE 7

Hydroquinone-bis-acryloyloxybenzoate prepared as in Example 1 is admixed with 0.5 percent by weight of Di-cup®, a polymerization catalyst comprised of 96–100 percent active dicumyl peroxide marketed by Hercules, Inc. The resulting powder admixture is molded and cured in a stainless steel mold of dimensions 1×3×0.02 inches at 180° C. for one hour under a pressure of 5000 psi using a Carver Laboratory Press Model C. The heat-cured material is cooled in the mold under pressure and found to exist as a biaxially oriented thermoset plastic composite.

EXAMPLE 8

Hydroquinone-bis-acryloyloxybenzoate (75 parts by weight) and hexanediol diacrylate (25 parts by weight) are mixed with 0.5 percent by weight of Di-cup®. The admixture is cured according to the procedure of Example 7 to yield a product comprised of a hard, tough, biaxially oriented plastic composite having clear transparent domains.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A thermoset resin comprised of heat-cured segments derived from acrylic-terminated monomers capable of forming an anisotropic melt phase of the formula:

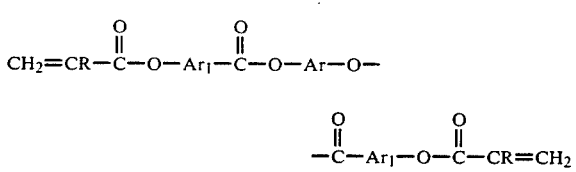

wherein Ar is a divalent radical comprising at least one aromatic ring, $Ar_1$ is a divalent radical selected from the group consisting of phenylene, naphthylene, biphenylene and mixtures thereof and R is selected from the group consisting of hydrogen and methyl, with at least some of the hydrogen atoms present upon the aromatic rings in said divalent radicals optionally being replaced by substitution selected from the group consisting of an alkyl group of 1 to 4 carbon atoms, an alkoxy group of 1 to 4 carbon atoms, halogen, phenyl, substituted phenyl and mixtures thereof.

2. A thermoset resin comprised of heat-cured segments derived from the monomer of claim 1 wherein Ar is selected from the group consisting of

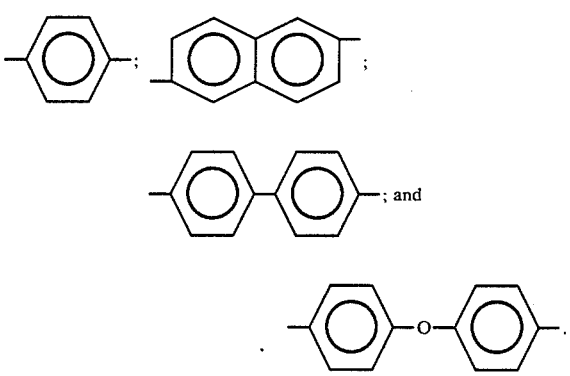

3. A thermoset resin comprised of heat-cured segments derived from the monomer of claim 1 wherein Ar is

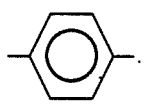

4. A thermoset resin comprised of heat-cured segments derived from the monomer of claim 1 wherein Ar is 5. A thermoset resin comprised of heat-cured segments derived from the monomer of claim 1 wherein Ar is

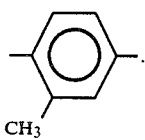

6. A thermoset resin comprised of heat-cured segments derived from the monomer of claim 1 wherein Ar is

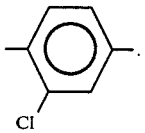

7. A thermoset resin comprised of heat-cured segments derived from the monomer of claim 1 wherein Ar is

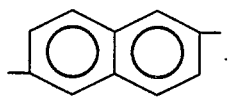

8. A thermoset resin comprised of heat-cured segments derived from the monomer of claim 1 wherein Ar is

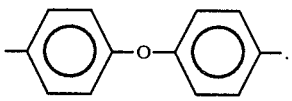

9. A thermoset resin comprised of heat-cured segments derived from the monomer of claim 1 wherein R is hydrogen in each instance.

10. A thermoset resin comprised of heat-cured segments derived from the monomer of claim 1 wherein $Ar_1$ is

11. A thermoset resin comprised of heat-cured segments derived from hydroquinone-bis-acryloyloxybenzoate.

12. A thermoset resin comprised of heat-cured segments derived from 2,6-dihydroxynaphthalene-bis-acryloyloxybenzoate.

13. A thermoset resin comprised of heat-cured segments derived from 4,4'-biphenol-bis-acryloyloxybenzoate.

14. A thermoset resin comprised of heat-cured segments derived from chlorohydroquinone-bis-acryloyloxybenzoate.

15. A thermoset resin comprised of heat-cured segments derived from 4,4'-oxybiphenol-bis-acryloyloxybenzoate.

16. A thermoset resin comprised of heat-cured segments derived from methylhydroquinone-bis-acryloyloxybenzoate.

* * * * *